(12) United States Patent
Ohta et al.

(10) Patent No.: US 8,944,599 B2
(45) Date of Patent: Feb. 3, 2015

(54) OPHTHALMOLOGIC APPARATUS, AND OPHTHALMOLOGIC CONTROL METHOD AND PROGRAM

(71) Applicant: Canon Kabushiki Kaisha, Tokyo (JP)

(72) Inventors: Koichi Ohta, Kawasaki (JP); Toshiaki Okumura, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/055,737

(22) Filed: Oct. 16, 2013

(65) Prior Publication Data

US 2014/0111770 A1 Apr. 24, 2014

(30) Foreign Application Priority Data

Oct. 18, 2012 (JP) .................................. 2012-230784

(51) Int. Cl.
*A61B 3/14* (2006.01)
*A61B 3/10* (2006.01)

(52) U.S. Cl.
USPC ........................... 351/208; 351/211; 351/205

(58) Field of Classification Search
USPC .................................................. 351/200–246
See application file for complete search history.

(56) References Cited

U.S. PATENT DOCUMENTS

| 8,721,079 B2 * | 5/2014 | Uchida et al. ................. 351/208 |
| 2001/0028440 A1 * | 10/2001 | Iwanaga ........................ 351/208 |
| 2007/0258045 A1 * | 11/2007 | Yamaguchi et al. .......... 351/221 |

FOREIGN PATENT DOCUMENTS

| JP | 2008295972 A | 12/2008 |
| JP | 4428987 B2 | 3/2010 |

\* cited by examiner

*Primary Examiner* — Mohammed Hasan
(74) *Attorney, Agent, or Firm* — Canon USA Inc. IP Division (57) ABSTRACT

An ophthalmologic apparatus, when an output result of an imaging unit provided in an optical path of an imaging optical system satisfies a predetermined condition, stops controlling a driving unit in at least one direction based on a positional relationship of an image of the light flux, which has been reflected by a cornea of the subject's eye and regulated by a light flux regulation unit provided in the optical path of the imaging optical system, and maintains the control of the driving unit in the other directions.

20 Claims, 11 Drawing Sheets

STATE WHERE ALIGNMENT IN Z-AXIS DIRECTION
(BACK-AND-FORTH DIRECTION) HAS BEEN ACHIEVED

FIG. 4B

STATE WHERE ALIGNMENT IN Z-AXIS DIRECTION
(BACK-AND-FORTH DIRECTION) IS POOR (TOO FAR)

WHEN ALIGNMENT PRISM DIAPHRAGM IS INSERTED

FIG. 6B

WHEN ALIGNMENT PRISM DIAPHRAGM IS RETRACTED

OPHTHALMOLOGIC APPARATUS, AND OPHTHALMOLOGIC CONTROL METHOD AND PROGRAM

BACKGROUND OF THE INVENTION

1. Field of the Invention

The present invention relates to an ophthalmologic apparatus, which acquires information specific to a subject's eye (e.g., eye refractive power, intraocular pressure, and a fundus image), and an ophthalmologic control method and program.

2. Description of the Related Art

In a recent ophthalmologic apparatus, an index light flux for alignment has been projected onto a subject's eye, to generate a reference index image for alignment. The reference index image has been used to automatically drive a measurement unit in the ophthalmologic apparatus in up-and-down and right-and-left directions and in a back-and-forth direction with respect to the subject's eye. An ophthalmologic apparatus having a function of aligning a subject's eye and a measurement unit with each other by so-called automatic alignment has been the mainstream.

The ophthalmologic apparatus having such an automatic alignment function has a manual alignment function for an operator to perform a driving operation in up-and-down and right-and-left directions and in a back-and-forth direction of an optometric unit to move a measurement unit to a desired position in addition to the alignment by the automatic alignment. As to a manual alignment function, Japanese Patent No. 4428987 discusses an apparatus which shifts to a measurement mode for performing automatic alignment in a back-and-forth direction and performing manual alignment in up-and-down and right-and-left directions, when a measurement error is continued in automatic alignment.

As a case where alignment by automatic alignment cannot be performed, Japanese Patent Application Laid-Open No. 2008-295972 discusses coping with a case where a light receiving amount of noise light other than an image of a light flux for alignment reaches a threshold value for a subject's eye having a small pupil diameter. More specifically, an apparatus which detects a luminance distribution of an alignment index in a captured anterior eye image and changes a projection light amount of the alignment index or the sensitivity of a detection unit, is discussed for a subject's eye having a small pupil diameter.

However, in such an ophthalmologic apparatus which performs alignment by automatic alignment, if a subject's eye has a low cornea reflectance due to a disease, an image caused by cornea reflection of a light flux for alignment becomes dark so that alignment cannot be performed. Alternatively, if a subject's eye has a small pupil diameter, noise light other than an image of a light flux for alignment becomes bright so that alignment cannot be performed.

SUMMARY OF THE INVENTION

The present invention is directed to performing alignment without significantly deteriorating precision even if the reflectance on a cornea of a subject's eye is relatively small and if the pupil diameter of the subject's eye is relatively small.

According to an aspect of the present invention, an ophthalmologic apparatus includes an acquisition unit configured to acquire information specific to a subject's eye, a driving unit configured to drive the acquisition unit for alignment with the subject's eye, a projection unit configured to project a light flux for alignment onto a cornea of the subject's eye, an anterior eye illumination unit configured to illuminate an anterior eye portion of the subject's eye, an imaging unit configured to image the anterior eye portion of the subject's eye via an imaging optical system, a light flux regulation unit provided in an optical path of the imaging optical system, and a drive control unit configured to stop controlling the driving unit in at least one direction based on a positional relationship of an image of the light flux, which has been reflected by the cornea of the subject's eye and regulated by the light flux regulation unit, and to maintain the control of the driving unit in the other directions when an output result of the imaging unit satisfies a predetermined condition.

According to another aspect of the present invention, an ophthalmologic control method includes acquiring information specific to a subject's eye using an acquisition unit, driving the acquisition unit for alignment with the subject's eye using a driving unit, projecting a light flux for alignment onto a cornea of the subject's eye, illuminating an anterior eye portion of the subject's eye, imaging the anterior eye portion of the subject's eye via an imaging optical system using an imaging unit, and stopping controlling the driving unit in at least one direction based on a positional relationship of an image of the light flux, which has been reflected by the cornea of the subject's eye and regulated by the light flux regulation unit provided in an optical path of the imaging optical system, and maintaining the control of the driving unit in the other directions when an output result of the imaging unit satisfies a predetermined condition.

According to an exemplary embodiment of the present invention, alignment can be performed without significantly deteriorating precision even if the reflectance on a cornea of a subject's eye is relatively small (if there is little signal light) and if the pupil diameter of the subject's eye is relatively small (if there is much noise light).

Further features of the present invention will become apparent from the following description of exemplary embodiments with reference to the attached drawings.

DESCRIPTION OF THE EMBODIMENTS

If a light receiving amount of an image of a light flux for alignment does not reach a threshold value or if a light receiving amount of noise light other than the image of the light flux reaches the threshold value, the light flux for alignment cannot be detected so that control of a driving unit for alignment in a back-and-forth direction and in up-and-down and right-and-left directions becomes difficult. In such a case, the control of the driving unit for alignment is stopped in the back-and-forth direction, and the alignment is performed by observing an anterior eye image with its depth of focus being shallow in the back-and-forth direction. The control of the driving unit for alignment is maintained based on a positional relationship of the image of the light flux, which has been reflected by a cornea, from an anterior eye illumination unit in the up-and-down and right-and-left directions.

(Apparatus Body)

Figure 2:
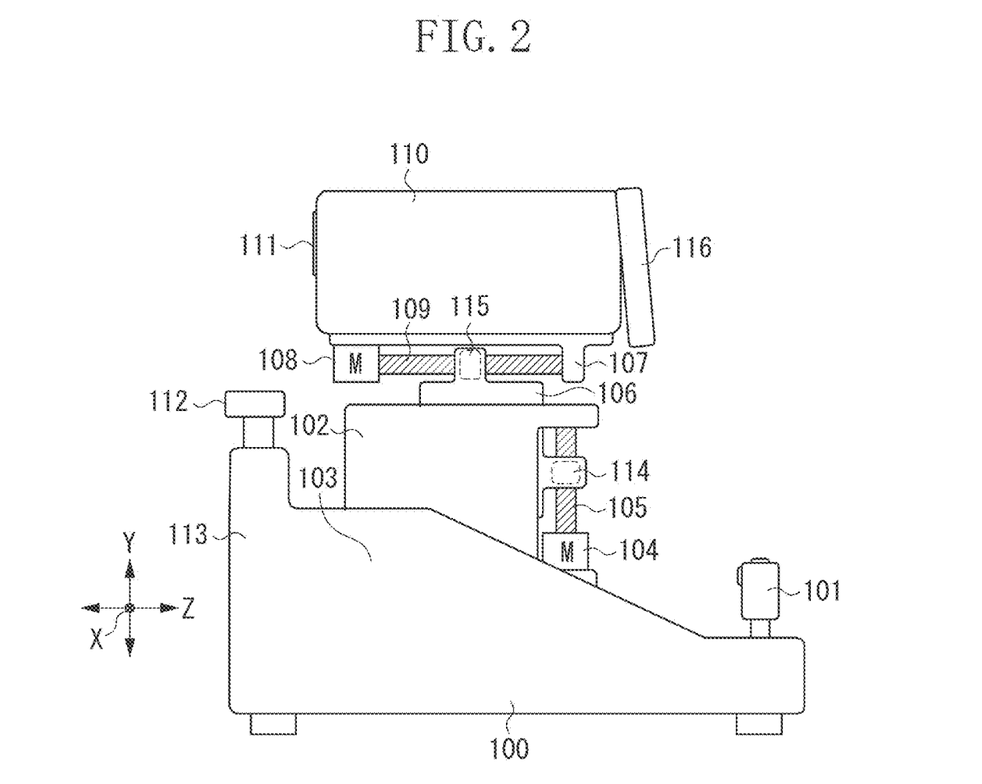
FIG. 2 is an external view of the eye refractive power meter according to the exemplary embodiment of the present invention.

FIG. 2 illustrates a schematic configuration of an eye refractive power meter serving as an ophthalmologic apparatus according to a first exemplary embodiment of the present invention. A frame 102 is movable in a right-and-left direction (hereinafter referred to as an X-axis direction) with respect to a base 100. An X-axis direction driving mechanism includes an X-axis driving motor 103 fixed on the base 100, a feed screw (not illustrated) connected to an output shaft of the motor 103, and a nut (not illustrated) fixed to the frame 102 while being movable in the X-axis direction on the feed screw. The frame 102 moves in the X-axis direction via the feed screw and the nut by rotation of the motor 103.

A frame 106 is movable in an up-and-down direction (hereinafter referred to as a Y-axis direction) with respect to the frame 102. A Y-axis direction driving mechanism includes a Y-axis driving motor 104 fixed on the frame 102, a feed screw 105 connected to an output shaft of the motor 104, and a nut 114 fixed to the frame 106 while being movable in the Y-axis direction on the feed screw 105. The frame 106 moves in the Y-axis direction via the feed screw 105 and the nut 114 by rotation of the motor 104.

A frame 107 is movable in a back-and-forth direction (hereinafter referred to as a Z-axis direction) with respect to the frame 106. A Z-axis direction driving mechanism includes a Z-axis driving motor 108 fixed on the frame 107, a feed screw 109 connected to an output shaft of the motor 108, and a nut 115 fixed to the frame 106 while being movable in the Z-axis direction on the feed screw 109.

The frame 107 moves in the Z-axis direction via the feed screw 109 and the nut 115 by rotation of the motor 108. A measurement unit 110, which measures eye refractive power, is fixed as a specific information acquisition unit on the frame 107.

A light source (not illustrated) for performing alignment and a light source unit 111 for measuring a cornea curvature are provided at an end on the side of a subject of the measurement unit 110.

The frame 100 is provided with a joystick 101 serving as an operation member for aligning the measurement unit 110 with respect to the subject's eye E. During the alignment, an operator tilts the joystick 101 in the X-axis direction and in the Z-axis direction to perform position adjustment in each of the directions, and rotates the joystick 101 to perform position adjustment in the Y-axis direction.

When refractive power is measured, the subject can fix a position of the subject's eye E by putting his/her chin on a chin rest 112 and pressing his/her forehead against a forehead rest portion of a face rest frame (not illustrated) fixed to the frame 100. A chin rest driving mechanism 113 makes the chin rest 112 adjustable in the Y-axis direction according to the size of the subject's face.

A liquid crystal display (LCD) monitor 116 serving as a display member for observing the subject's eye E is provided at an end on the side of the operator of the measurement unit 110 so that a measurement result can be displayed thereon.

(Measurement Unit)

Figure 1A:
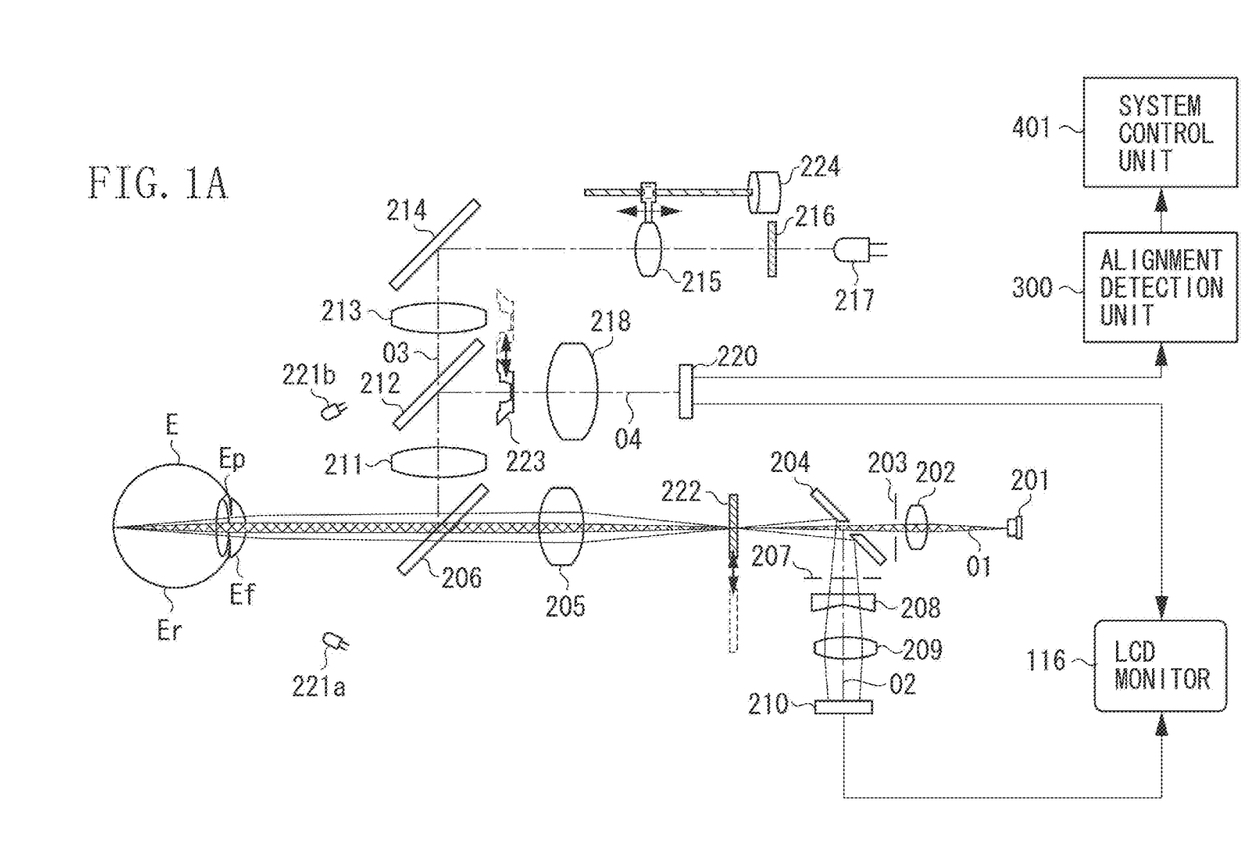
FIGS. 1A, 1B, and 1C respectively illustrate an arrangement of an optical system of a measurement unit in an eye refractive power meter according to an exemplary embodiment of the present invention, an anterior eye image to be captured in a first alignment mode, and an anterior eye image to be captured in a second alignment mode.

FIG. 1A illustrates an arrangement of an optical system inside of the measurement unit 110. A lens 202, a diaphragm 203 substantially conjugate with a pupil Ep of the subject's eye E, a perforated mirror 204, and a lens 205 are sequentially arranged on an optical path 01 leading to the subject's eye E from an eye refractive power measurement light source 201 which irradiates light having a wavelength of 880 nm. Further, a dichroic mirror 206, which totally reflects infrared and visible light having a wavelength of less than 880 nm and partially reflects a light flux having a wavelength of 880 nm or more from the side of the subject's eye E, is arranged on the optical path 01.

A diaphragm 207 substantially conjugate with the pupil Ep and including a ring-shaped slit, a light flux spectral prism 208, a lens 209, and an image sensor 210 are sequentially arranged on an optical path 02 in a reflection direction of the perforated mirror 204.

The above-mentioned optical system is for measuring eye refractive power. The lens 202 forms a primary image from a light flux, which has been emitted from the measurement light source 201, in front of the lens 205 while the diaphragm 203 narrows the light flux. The light flux is projected onto a pupil center of the subject's eye E after passing through the lens 205 and the dichroic mirror 206.

The projected light flux is reflected by a fundus Er of the subject's eye E, and the fundus reflected light flux is incident on the lens 205 again after passing through a pupil periphery. The incident light flux is reflected by the periphery of the perforated mirror 204 after passing through the lens 205.

The reflected light flux is pupil-separated by the diaphragm 207, substantially conjugate with the pupil Ep of the subject's eye E and including the ring-shaped slit, and the light flux spectral prism. 208, and is projected as a ring image onto a light receiving surface of the image sensor 210.

If the subject's eye E is an emmetropic eye, the ring image forms a predetermined circle. If the subject's eye E is a myopic eye, the ring image forms a circle smaller than that formed by the emmetropic eye. If the subject's eye E is a hypermetropic eye, the ring image forms a circle larger than that formed by the emmetropic eye and projected.

If the subject's eye E is astigmatic, the ring image forms an ellipse. An angle formed between a horizontal axis and the ellipse becomes an astigmatic axis angle. Refractive power is found based on a coefficient of the ellipse.

(Guidance of Diopter by Fixation Target)

A fixation target projection optical system and an alignment light receiving optical system, which is used for both observation of an anterior eye portion of the subject's eye E and alignment detection, are arranged in a reflection direction of the dichroic mirror 206.

A lens 211, a dichroic mirror 212, a lens 213, a reflecting mirror 214, a lens 215, a fixation target 216, and a fixation target illumination light source 217 are sequentially arranged on an optical path 03 of the fixation target projection optical system.

At the time of fixation guidance, the fixation target illumination light source 217, which has been turned on, illuminates the fixation target 216 with a projection light flux from behind. The projection light flux is projected onto the fundus Er of the subject's eye E via the lens 215, the reflecting mirror 214, the lens 213, the dichroic mirror 212, and the lens 211.

The lens 215 guides the diopter of the subject's eye E, and is movable in an optical axis direction by a fixation guiding motor 224 to realize a fogging state.

(Anterior Eye Observation and Alignment Using Index)

An alignment prism diaphragm 223 serving as a light flux regulation unit to be inserted and separated by an insertion and separation solenoid (not illustrated), a lens 218, and an image sensor 220 are sequentially arranged on an optical path 04 in a reflection direction of the dichroic mirror 212. By insertion and separation of the alignment prism diaphragm 223, alignment and anterior eye observation or transillumination observation can be performed, respectively, when the alignment prism diaphragm 223 is on the optical path 04 and when it is retracted from the optical path 04.

Figure 3:
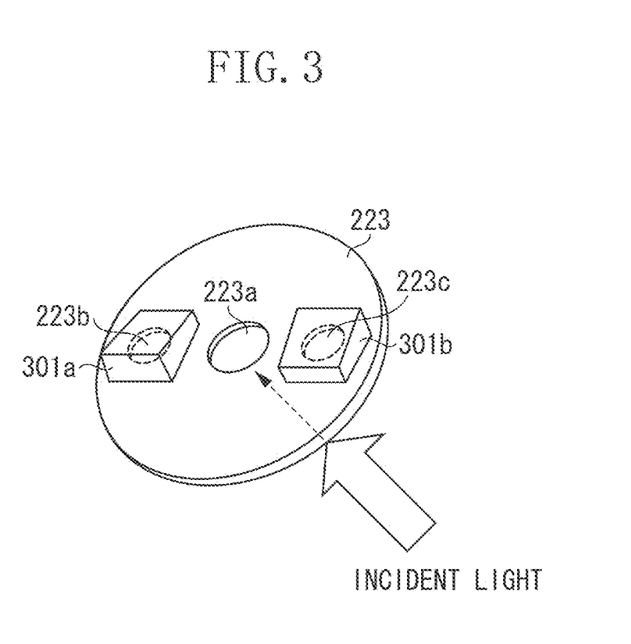
FIG. 3 is a perspective view of an alignment prism diaphragm according to the exemplary embodiment of the present invention.

FIG. 3 illustrates a shape of the alignment prism diaphragm 223 as viewed from a side opposite to the incident side. On the incident side, a disk-shaped diaphragm plate has three openings 223a, 223b, and 223c. Alignment prisms 301a (on the right side of incident light) and 301b (on the left side of incident light), which displace only a light flux having a wavelength in the vicinity of 880 nm in mutually opposite directions, are affixed to the backs of the openings 223b and 223c on both sides.

Referring to FIG. 1A again, anterior eye illumination light sources 221a and 221b, which irradiate an anterior eye portion with light of a wavelength of approximately 780 nm are arranged diagonally in front of the anterior eye portion of the subject's eye E (a second irradiation unit) separately from a first irradiation unit (described below), which irradiates the subject's eye E with a parallel light flux. The anterior eye illumination light sources 221a and 221b illuminate the anterior eye portion of the subject's eye E.

An image of the illuminated anterior eye portion is formed on a light receiving sensor surface of the image sensor 220 via the dichroic mirror 206, the lens 211, the dichroic mirror 212, the opening 223a at the center of the alignment prism diaphragm 223, and the lens 218. The lenses 211 and 218 function as an imaging optical system for imaging the anterior eye portion.

A light source serving as the first irradiation unit for alignment detection is also used as the measurement light source 201 for measuring eye refractive power. During alignment, a diffusion plate insertion and separation solenoid (not illustrated) inserts a semi-transparent diffusion plate 222 into the optical path 01. A position into which the diffusion plate 222 is to be inserted is a substantially focal position of the lens 205. Thus, an image of the measurement light source 201 is projected once onto the diffusion plate 222, and the projected image serves as a secondary light source and is projected as a thick parallel light flux toward the subject's eye E from the lens 205 (the first irradiation unit).

Figure 1B:
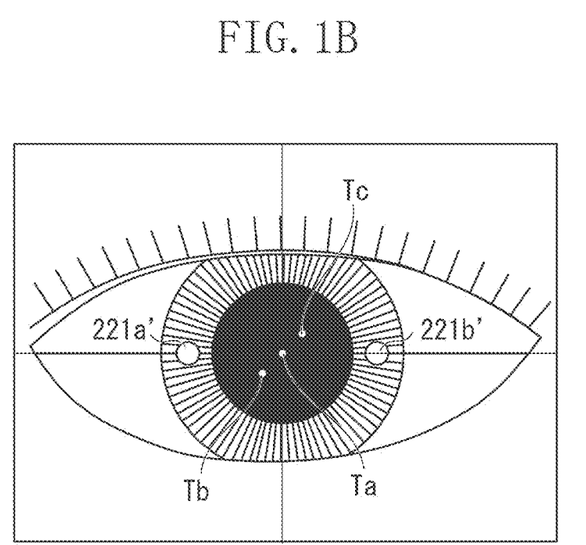

The parallel light flux is reflected by a cornea Ef of the subject's eye E, to form a spot image (a virtual image) due to cornea reflection at a cornea focal position. The cornea reflected light flux is partially reflected again by the dichroic mirror 206, and is reflected by the dichroic mirror 212 via the lens 211. The reflected light flux passes through the opening 223a of the alignment prism diaphragm 223, the alignment prism 301a and the opening 223b, and the alignment prism 301b and the opening 223c. Thus, the light flux is converged on the lens 218, and is formed as index images Ta, Tb, and Tc on the image sensor 220 (FIG. 1B).

A light flux having a wavelength of 780 nm or more from each of the anterior eye illumination light sources 221a and 221b passes through the opening 223a at the center of the alignment prism diaphragm 223. Thus, the imaging lens 218 forms an image of the anterior eye portion, which has been illuminated by the anterior eye illumination light sources 221a and 221b, on the image sensor 220 via the opening 223a of the alignment prism diaphragm 223 after passing through an observation optical system, like through a path of the light flux reflected by the cornea Ef. More specifically, an anterior eye image including an iris of the subject's eye E and cornea reflected images 221a' and 221b' of the anterior eye illumination light sources 221a and 221b is formed on the image sensor 220 (FIG. 1B).

(Alignment Operation)

Figure 1C:
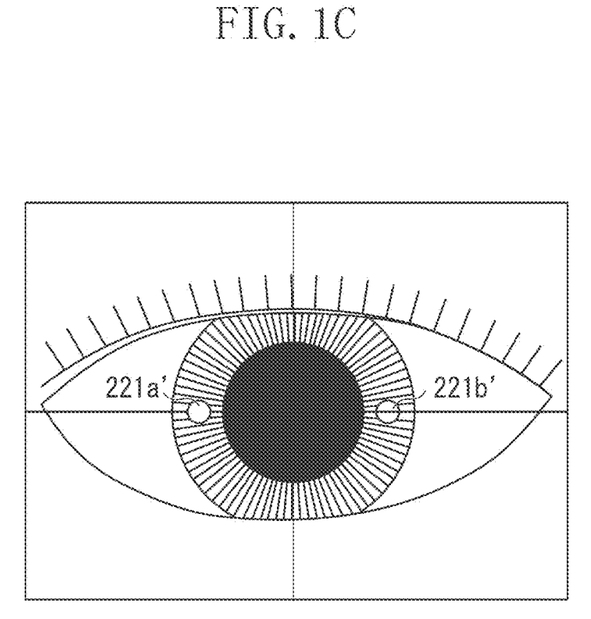

During normal alignment (during a first alignment mode), alignment control is performed so that the center of an anterior eye image illustrated in FIG. 1C matches an apparatus reference in the X-axis direction and in the Y-axis direction. Alignment control is performed so that respective positions of the three index images Ta, Tb, and Tc by the first irradiation unit line up in the Y-axis direction (vertical direction), as illustrated in FIG. 4A, in the Z-axis direction.

Figure 4A:
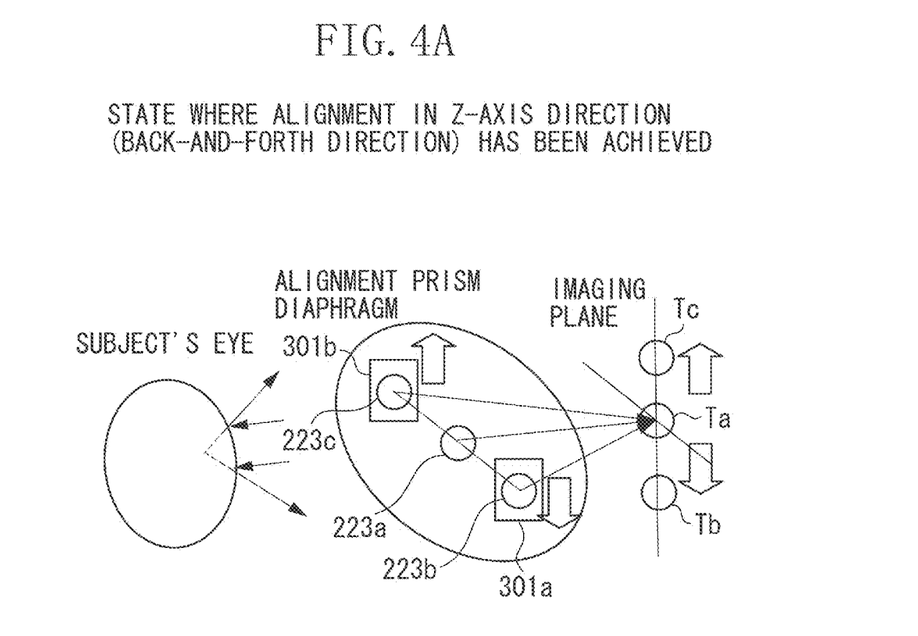
FIGS. 4A, 4B, and 4C respectively illustrate a state where alignment in a back-and-forth direction is achieved using an alignment prism diaphragm, a state where alignment is too far, and a state where alignment is too close.

If the alignment prisms 301a and 301b do not exist in FIG. 4A, light fluxes, which have passed through three openings, i.e., the opening 223a at the center and the plurality of openings 223b and 223c at both ends, converge on one point. However, the light fluxes are displaced in the Y-axis direction due to the existence of two prisms, i.e., alignment prisms 301a and 301b, corresponding to the openings 223b and 223c respectively at both ends. More specifically, the light flux, which passes through the alignment prism 301a, is displaced in a direction in which the wedge thickness of the alignment prism 301a increases (in a downward direction). On the other hand, the light flux, which passes through the alignment prism 301b, the wedge thickness of which increases in an opposite direction to that of the alignment prism 301a, is displaced in a direction in which the wedge thickness of the alignment prism 301b increases (in an upward direction).

Thus, in a state where alignment in the Z-axis direction is achieved, as illustrated in FIG. 4A, the three index images Ta, Tb, and Tc line up in the Y-axis direction. Light fluxes from the anterior eye portion, which has been illuminated by the anterior eye illumination light sources 221a and 221b, do not pass through the alignment prisms 301a and 301b separating wavelength. Therefore, an anterior eye image, which is displaced with the index images Ta, Tb, and Tc in the Y-axis direction, is not formed.

Figure 4B:
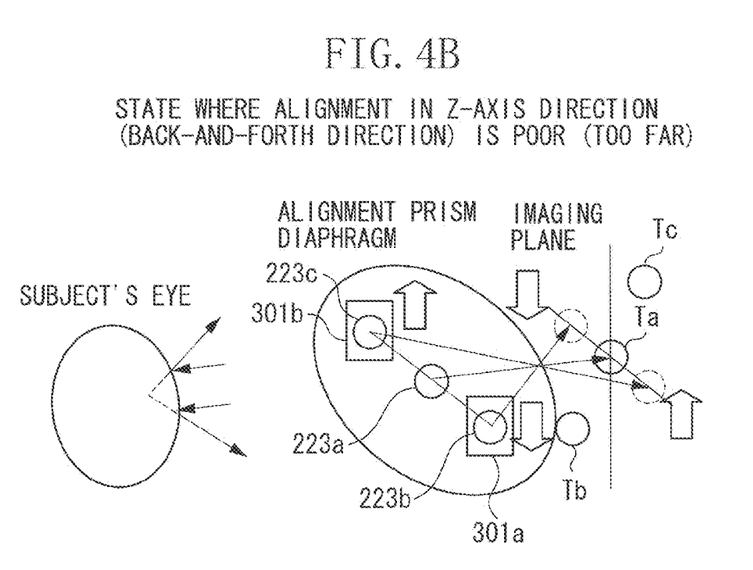

In FIG. 4B, in a state where alignment is poor (too far) in the Z-axis direction, if the alignment prisms 301a and 301b do not exist, light fluxes, which have passed through the each openings 223a, 223b, and 223c, are separated from one another in the X-axis direction. The light fluxes are displaced in the Y-axis direction due to the existence of the alignment prisms 301a and 301b, and the index images Ta, Tb, and Tc rotate in a clockwise direction from the Y-axis direction.

Figure 4C:
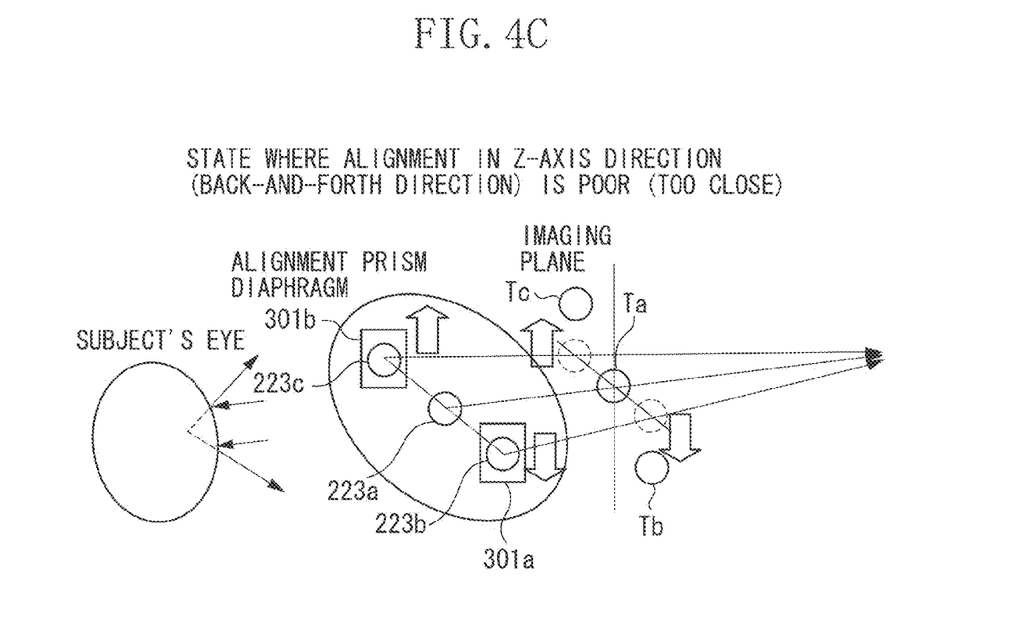

In FIG. 4C, in a state where alignment is poor (too close) in the Z-axis direction, if the alignment prisms 301a and 301b do not exist, light fluxes, which have passed through the each openings 223a, 223b, and 223c, are separated from one another in the X-axis direction. The light fluxes are displaced in the Y-axis direction due to the existence of the alignment prisms 301a and 301b, and the index images Ta, Tb, and Tc rotate in a counterclockwise direction from the Y-axis direction.

When the three index images Ta, Tb, and Tc can be detected, a system control unit 401 controls a motor driving circuit 413, and drives the measurement unit 110 in the Y- and X-axis directions so that the index image Ta at the center matches its center. The system control unit 401 then drives the measurement unit 110 in the Z-axis direction so that the index images Tb and Tc are arranged in the Y-axis direction with respect to the index image Ta, and completes the alignment with the three index images Ta, Tb, and Tc lining up in the Y-axis direction.

(Overall System Control)

Figure 5:
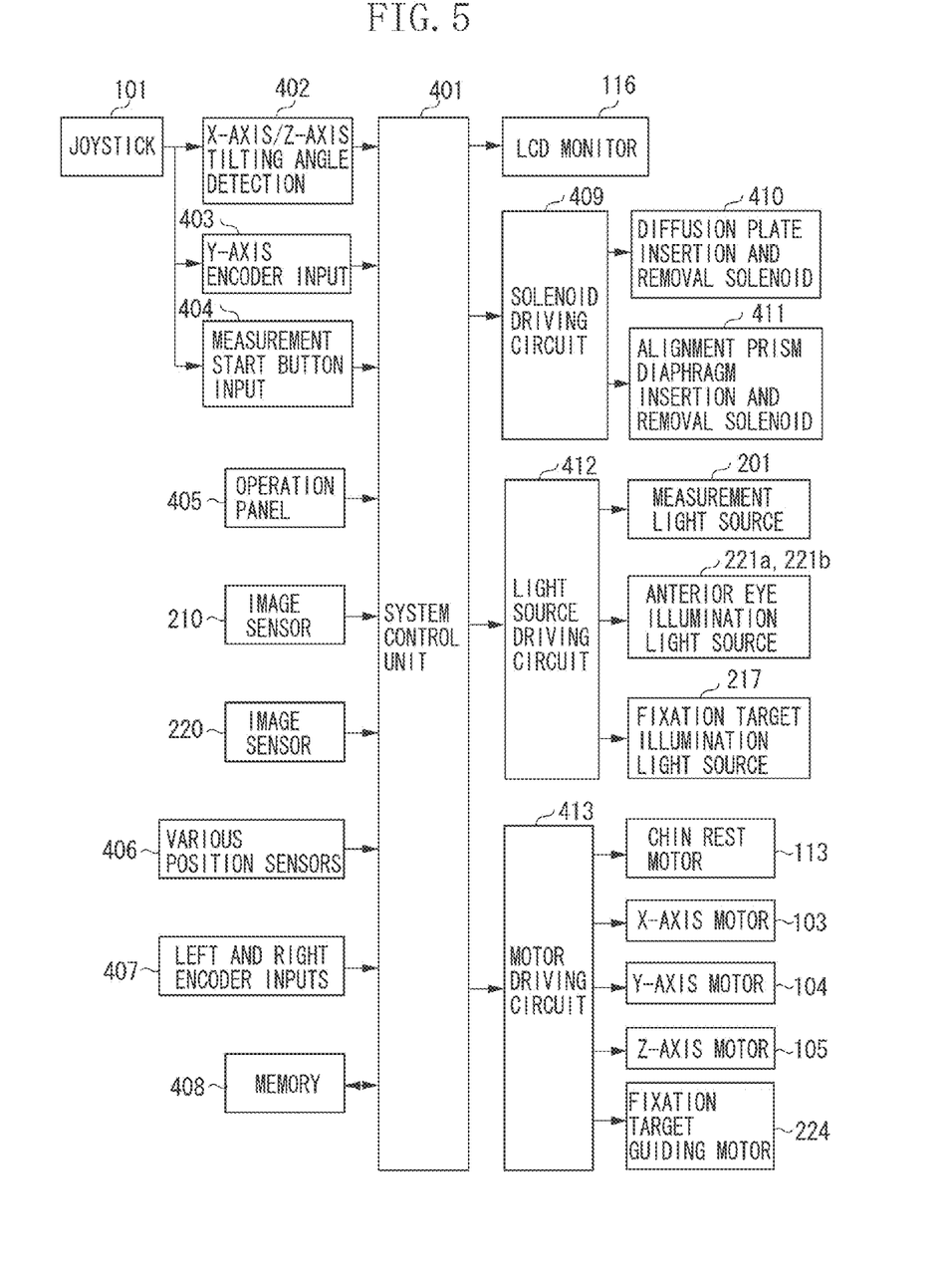
FIG. 5 is a system block diagram of the eye refractive power meter according to the exemplary embodiment of the present invention.

FIG. 5 is a system block diagram. The system control unit 401, which controls the entire system, includes a program storage unit, a data storage unit which stores data for correcting eye refractive power values, an input/output control unit which controls input/output to/from various devices, and an arithmetic processing unit which calculates data obtained from the various devices.

The joystick 101, which aligns the measurement unit 110 with a subject's eye E and starts measurement, is connected to the system control unit 401 via an X-axis/Z-axis tilting angle detection 402 when the joystick 101 is tilted in the Z- and X-axis directions, a Y-axis encoder input 403 when the joystick 101 is rotated, and a measurement start button input 404 when a measurement start button is pressed. A printing button and a chin rest up-and-down button are arranged in a operation panel 405 (not illustrated) on the base 100, and a signal is notified to the system control unit 401 when the button is pressed.

An anterior eye image of the subject's eye E, which has been captured by the image sensor 220, is stored in a memory 408. A pupil Ep of the subject's eye E and cornea reflected images are extracted from the image stored in the memory 408, to perform alignment detection. The anterior eye image of the subject's eye E, which has been captured by the image sensor 220, is combined with characters and graphic data, and an anterior eye image and a measured value are displayed on an LCD monitor 116.

A ring image for calculating eye refractive power, which has been captured by the image sensor 210, is stored in the memory 408.

Each of a diffusion plate insertion and removal solenoid 410 and an alignment prism diaphragm insertion and removal solenoid 411 is controlled to be driven in response to an instruction from the system control unit 401 via a solenoid driving circuit 409. A X-axis motor 103, a Y-axis motor 104, a Z-axis motor 105, a chin rest motor 113, and a fixation target guiding motor 224 are driven in response to an instruction from the system control unit 401 via the motor driving circuit 413.

The measurement light source 201, the anterior eye illumination light sources 221*a* and 221*b*, and a fixation target light source 217 control lighting, extinction, and light amount change in response to an instruction from the system control unit 401 via a light source driving circuit 412.

An operation in an apparatus having the above-mentioned configuration will be described. A description of alignment is omitted because it has already been described. To measure eye refractive power, the system control unit 401 retracts the diffusion plate 222, which has been inserted into the optical path 01 for automatic alignment, from the optical path 01. The system control unit 401 adjusts an amount of light from the measurement light source 201, to project a measurement light flux onto the fundus Er of the subject's eye E. Reflected light from the fundus Er is received by the image sensor 210 after passing through the optical path 02. The ring diaphragm 207 projects a captured fundus image in a ring shape by refractive power of the subject's eye E. Such a ring image is stored in the memory 408.

Barycentric coordinates of the ring image stored in the memory 408 are calculated, to find an equation of an ellipse using a known method. A major diameter and a minor diameter of the found ellipse and a tilting of a major-diameter axis are calculated, to calculate eye refractive power of the subject's eye E. The fixation target guiding motor 224 is driven via a motor driving circuit 413 using the calculated eye refractive power value to a position corresponding to the eye refractive power value, to move the lens 215, and to present the fixation target 216 on the subject's eye E using refractivity corresponding to the refractivity of the subject's eye E.

The lens 215 is then moved to a distance by a predetermined amount, the fixation target 216 is fogged, and the measurement light source 201 is turned on again, to measure refractive power. A final measured value at which the refractive power is stabilized can be obtained by repeating in order the measurement of the refractive power, the fogging of the fixation target 216, and the measurement of the refractive power.

(Second Alignment Mode)

Usually, the measurement of the eye refractive power is thus ended. However, if an output result of an imaging unit satisfies a predetermined condition, for example, if the cornea of the subject's eye E has a low reflectance, the index images for alignment Ta, Tb, and Tc become dark so that a light receiving amount of an image of a light flux for alignment does not reach a threshold value. If the subject's eye E has a small pupil diameter, for example, the index images Tb and Tc overlap the iris so that a light receiving amount of noise light other than the image of the light flux for alignment reaches the threshold value. Due to these causes, the index images may be undetectable so that automatic alignment cannot be completed.

If the reflectance of the cornea is low and outputs of the index images Ta, Tb, and Tc do not reach a threshold value as a case where automatic alignment cannot be completed in an automatic measurement mode of eye refractive power, an automatic alignment measurement mode is stopped. If the pupil diameter of the subject's eye E is small, and the index images Tb and Tc overlap the iris so that the light receiving amount of the noise light other than the image of the light flux for alignment reaches the threshold value, the automatic alignment measurement mode is stopped.

The automatic alignment measurement mode is automatically shifted to a manual alignment mode (second alignment mode). In the second alignment mode, alignment control is released, and an output of the imaging unit is observed using a monitor, to perform alignment (FIG. 1C).

More specifically, manual alignment is performed so that the anterior eye image is clearly visible by releasing the alignment control in the Z-axis direction. In the X-axis direction and in the Y-axis direction, automatic alignment is continued based on a positional relationship between images of light fluxes, which have been emitted from the anterior eye illumination light sources 221*a* and 221*b* and reflected by the cornea of the subject's eye E, while maintaining alignment control. However, the automatic alignment may be released and shifted to the manual alignment in the X-axis direction and in the Y-axis direction.

Figure 6A:
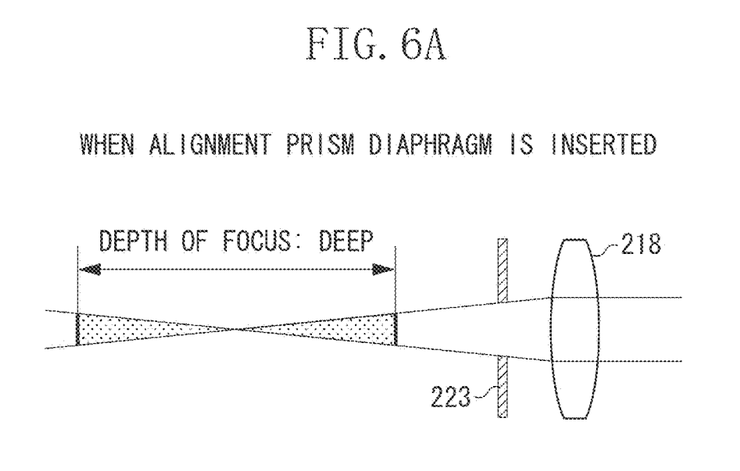
FIGS. 6A and 6B respectively illustrate a state where the depth of focus is deep when an alignment prism diaphragm is inserted and a state where the depth of focus is shallow when the alignment prism diaphragm is retracted.

The measurement light source 201 serving as the first irradiation unit is turned off. However, alignment becomes difficult because the depth of focus is deep, as illustrated in FIG. 6A, only by performing alignment using the second irradiation unit from using a combination of the first irradiation unit and the second irradiation unit. More specifically, if the alignment prism diaphragm 223 is on the optical path 04, as illustrated in FIG. 6A, the light flux is narrowed so that the depth of focus becomes deep. Therefore, a range in which front and back positions seem to be apparently matched is widened.

Figure 6B:
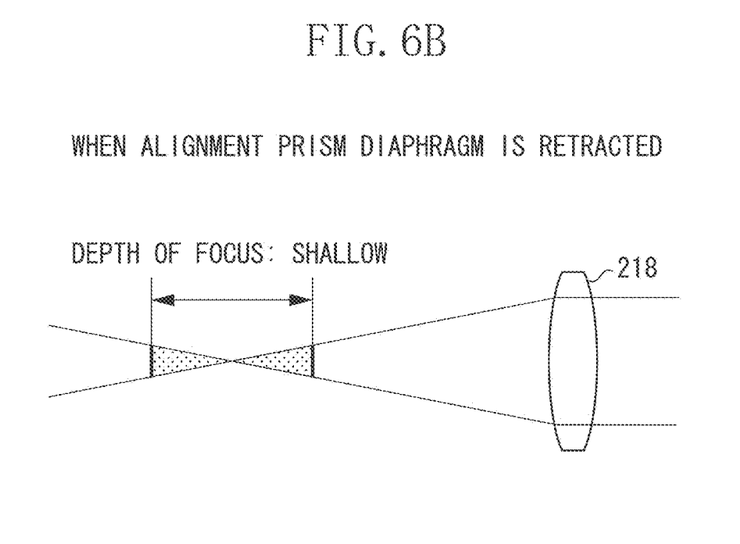

In the automatic alignment, there is no problem because front and back positions are matched depending on an alignment index. However, in the manual alignment, the operator needs to determine front and back positions and start measurement. Therefore, when the light flux is not narrowed so that the depth of focus is shallow, as illustrated in FIG. 6B, accurate alignment in the Z-axis direction can be achieved. In the second alignment mode, alignment in the Z-axis direction of an anterior eye image of the subject's eye E to be captured by the image sensor 220 using the iris can be easily performed by retracting the alignment prism diaphragm 223 from the optical path 04 to make the depth of focus of the anterior eye image shallow.

When the automatic alignment is switched to the manual alignment, an alignment operation can be further simply performed if the manual alignment is performed not in all the three X-, Y-, and Z-axis directions but only in the Z-axis direction by activating alignment control with the anterior eye image in the X- and Y-axis directions.

(Measurement Flow)

Figure 7:
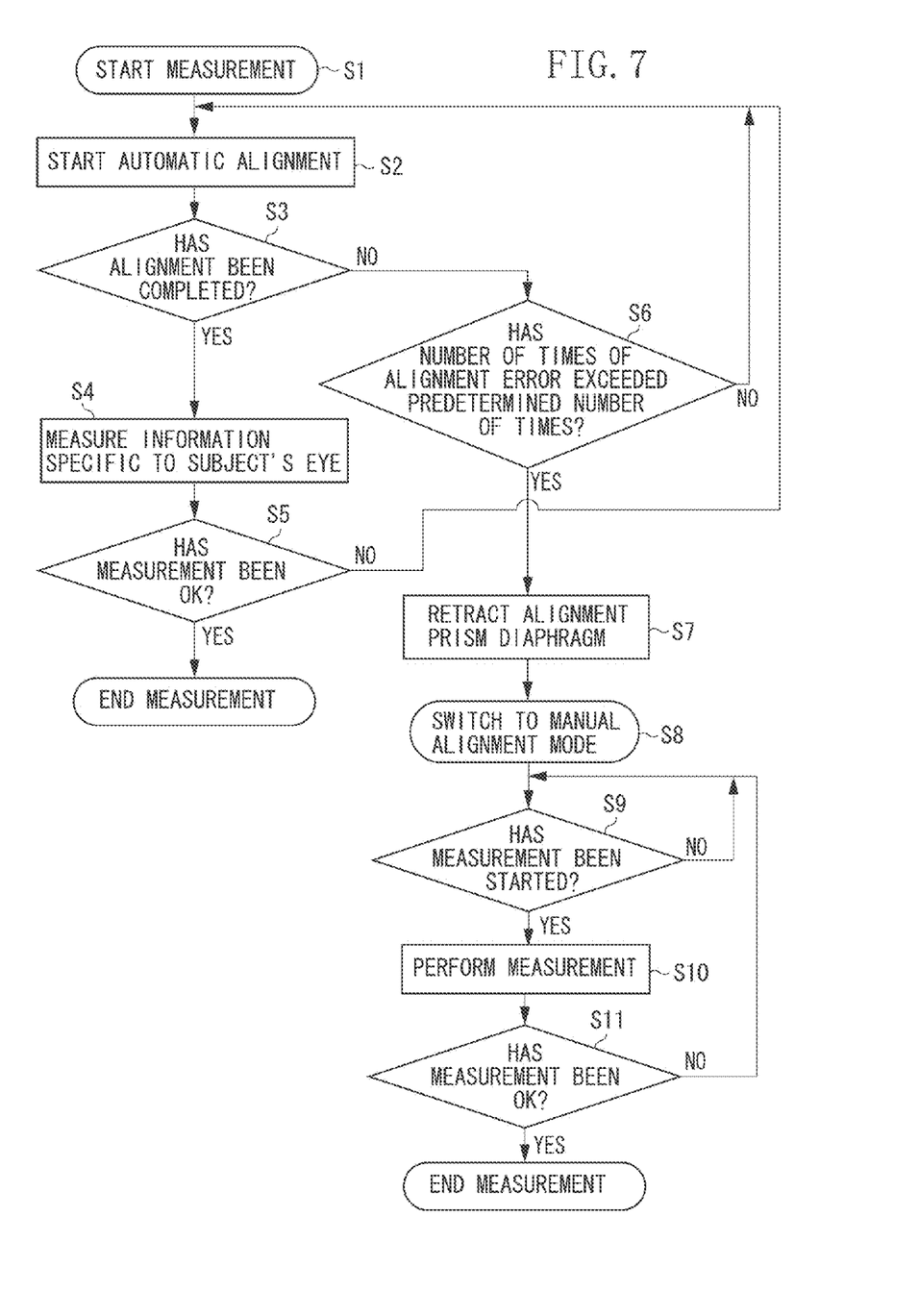
FIG. 7 is a flowchart of the eye refractive power meter according to the exemplary embodiment of the present invention.

A measurement flow will be described below with reference to FIG. 7. In step S1, an operator makes a subject put his/her chin on the chin rest 112, and adjusts the Y-axis direction of a subject's eye E using the driving mechanism 113 so that the subject's eye E has a set height. The operator operates the joystick 101 up to a position where cornea reflected images of the subject's eye E are displayed on the LCD monitor 116, which displays the subject's eye E, and presses the measurement start button. If the measurement start button is pressed, then in step S2, the system control unit 401 starts automatic alignment. The system control unit 401 extracts the cornea reflected images from an anterior eye image of the subject's eye E stored in the memory 408, to perform alignment using the above-mentioned alignment method.

In step S3, the system control unit 401 determines whether the alignment has been completed. If it is determined that the alignment has been completed (YES in step S3), the processing proceeds to step S4. If it is determined that the alignment has not yet been completed (NO in step S3), the system control unit 401 stores the number of times of an alignment error, and the processing proceeds to step S6. In step S4, the system control unit 401 measures information specific to the subject's eye E using a predetermined detection method, and the processing proceeds to step S5. In step S5, the system control unit 401 determines whether all of the predetermined measurements and the number of times of the predetermined measurements have been completed. If it is determined that the measurement has not yet been completed (No in step S5), the processing returns to step S2.

In step S6, the system control unit 401 determines whether the number of times of an alignment error in fine alignment exceeds a predetermined number of times. If the number of times of the alignment error does not exceed the predetermined number of times (NO in step S6), the processing returns to step S2. If the number of times of the alignment error exceeds the predetermined number of times (YES in step S6), the processing proceeds to step S7. In step S7, the system control unit 401 retracts the alignment prism diaphragm 223 from the optical path 04. In step S8, the system control unit 401 switches an automatic alignment mode to a manual alignment mode.

In step S9, the operator operates the joystick 101 to move a measurement position in the Y-, X-, and Z-axis directions or in the Z-axis direction, and the operator presses a measurement switch at the top of the joystick 101, and the system control unit 401 determines whether measurement has been started. If it is determined that the measurement has been started (YES in step S9), the processing proceeds to step S10.

In step S10, the system control unit 401 performs measurement using the above-mentioned eye refractive power measurement method, to store a ring image and a measured value in the memory 408. In step S11, the system control unit 401 determines whether the measurement has been OK. If the measurement has been OK (YES in step S11), the processing ends. If a measurement error has occurred (NO in step S11), the operator presses the measurement start button again so that the measurement can be performed again.

If the operator desires to perform automatic alignment again, the operator may press an automatic alignment changing switch (not illustrated), to insert the alignment prism diaphragm 223 into the optical path 04 so that the automatic alignment can be performed.

When the automatic alignment is thus switched to the manual alignment, to retract the alignment prism diaphragm 223 to make the depth of focus shallow so that the anterior eye image is easy to see, operability can be improved in alignment during measurement of the subject's eye E.

The present invention further includes a method, described below, with respect to the automatic alignment in step S2 and the manual mode in steps S7 and S8, as an ophthalmologic control method.

More specifically, the present invention includes, in the automatic alignment in step S2, projecting a light flux onto the subject's eye E for alignment with an acquisition unit, which acquires information specific to the subject's eye E, forming an image of an anterior eye portion of the subject's eye E on a predetermined surface using the imaging optical system, and performing alignment control based on an output of an imaging unit provided on the predetermined surface while the imaging optical system has a light flux regulation unit, which regulates a light flux reflected from the subject's eye E, provided in an optical path 04.

The present invention includes, in the manual mode in steps S7 and S8, performing alignment by releasing alignment control to observe the output of the imaging unit using a monitor while the light flux regulation unit is retracted to the outside of the optical path 04.

The present invention is also implemented as a computer-readable storage medium storing an ophthalmologic control program by performing the following processing, that is, supplying software (a program) for implementing the function of the above-mentioned exemplary embodiment to a system or an apparatus via a network or various recording media and causing a computer (or a central processing unit (CPU) or a microprocessing unit (MPU)) in the system or the apparatus to read out and execute the program.

(Modification Example 1)

While the eye refractive power measurement apparatus has been described in the above-mentioned exemplary embodiment, the present invention is not limited to this. The eye refractive power measurement apparatus may be a fundus camera which captures a fundus image, an ophthalmologic apparatus (an ophthalmologic optical coherence tomography (OCT) apparatus) which acquires a fundus tomographic image by optical interference of a near infrared laser, and a scanning laser ophthalmoscope (SLO) which acquires a fundus image using a confocus.

The eye refractive power measurement apparatus may be a blood flow meter which measures a blood flow of a fundus blood vessel, and a cornea shape measurement apparatus which measures the shape of a cornea. Further, the eye refractive power measurement apparatus is not limited to an ophthalmologic apparatus which optically acquires subject's eye information. The eye refractive power measurement apparatus may be an ophthalmotonometer which measures intraocular pressure information in non-contact by blowing an airstream, and an ophthalmologic apparatus which measures an ocular axial length with an ultrasonic probe contacted thereby.

(Modification Example 2)

While an opening and a prism are provided in this order along the optical path 04 for the alignment prism diaphragm 223, a prism and an opening may be conversely provided in this order.

(Modification Example 3)

While the light source 201 serving as the first irradiation unit may be turned off in the second alignment mode in the above-mentioned exemplary embodiment, the light source 201 may remain turned on.

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-230784 filed Oct. 18, 2012, which is hereby incorporated by reference herein in its entirety.

What is claimed is:

1. An ophthalmologic apparatus comprising:
   an acquisition unit configured to acquire information specific to a subject's eye;
   a driving unit configured to drive the acquisition unit for alignment with the subject's eye;
   a projection unit configured to project a light flux for alignment onto a cornea of the subject's eye;
   an anterior eye illumination unit configured to illuminate an anterior eye portion of the subject's eye;
   an imaging unit configured to image the anterior eye portion of the subject's eye via an imaging optical system;
   a light flux regulation unit provided in an optical path of the imaging optical system; and
   a drive control unit configured to stop controlling the driving unit in one direction of a plurality of directions based on a positional relationship of an image of the light flux, which has been reflected by the cornea of the subject's eye and regulated by the light flux regulation unit, and to maintain the control of the driving unit in the other directions of the plurality of directions when an output result of the imaging unit satisfies a predetermined condition.

2. The ophthalmologic apparatus according to claim 1, wherein the drive control unit stops control in a back-and-forth direction, and performs control in up-and-down and right-and-left directions based on the positional relationship of the image of the light flux, which has been reflected by the cornea of the subject's eye, from the anterior eye illumination unit when the output result of the imaging unit satisfies the predetermined condition.

3. The ophthalmologic apparatus according to claim 1, further comprising a unit configured to retract the light flux regulation unit to the outside of the optical path when the output result of the imaging unit satisfies the predetermined condition.

4. The ophthalmologic apparatus according to claim 1, wherein a light receiving amount of the image of the light flux, which has been output by the imaging unit, does not reach a threshold value when the output result of the imaging unit satisfies the predetermined condition.

5. The ophthalmologic apparatus according to claim 1, wherein a light receiving amount of noise light other than the image of the light flux, which has been output by the imaging unit, reaches a threshold value when the output result of the imaging unit satisfies the predetermined condition.

6. The ophthalmologic apparatus according to claim 1, wherein alignment in a back-and-forth direction is performed based on a signal of a joystick so that an anterior eye image to be displayed on a monitor connected to the imaging unit is made clear when the output result of the imaging unit satisfies the predetermined condition.

7. The ophthalmologic apparatus according to claim 1, wherein the light flux regulation unit includes a plurality of openings configured to regulate the light flux, which has been reflected from the subject's eye, and a plurality of prisms configured to respectively displace the light flux in opposite directions.

8. The ophthalmologic apparatus according to claim 1, wherein the light flux regulation unit includes three openings at its center and at its both ends configured to regulate the light flux, which has been reflected from the subject's eye, and two prisms corresponding to the openings at both the ends and configured to respectively displace the light flux in opposite directions.

9. A control method for an ophthalmologic apparatus including an acquisition unit configured to acquire information specific to a subject's eye, a driving unit configured to drive the acquisition unit for alignment with the subject's eye, a projection unit configured to project a light flux for alignment onto a cornea of the subject's eye, an anterior eye illumination unit configured to illuminate an anterior eye portion of the subject's eye, an imaging unit configured to image the anterior eye portion of the subject's eye via an imaging optical system, and a light flux regulation unit provided in an optical path of the imaging optical system, the control method comprising:
   stopping controlling the driving unit in one direction of a plurality of directions based on a positional relationship of an image of the light flux, which has been reflected by the cornea of the subject's eye and regulated by the light flux regulation unit provided in an optical path of the imaging optical system when an output result of the imaging unit satisfies a predetermined condition; and
   maintaining the control of the driving unit in the other directions of the plurality of directions.

10. A non-transitory computer-readable storage medium storing a program that causes a computer to perform the control method according to claim 9.

11. An ophthalmologic apparatus comprising:
an illuminating unit configured to illuminate an anterior eye portion of a subject's eye;
a light flux regulation unit configured to regulate a light flux provided in an optical path of an imaging optical system for imaging the anterior eye portion of the subject's eye; and
a retracting unit configured to retract the light flux regulation unit to the outside of the optical path when an output result of an imaging unit, which is provided in the optical path of the imaging optical system, satisfies a predetermined condition.

12. The ophthalmologic apparatus according to claim 11, wherein an intensity of at least an image of the light flux does not reach a threshold when the output result of the imaging unit satisfies the predetermined condition.

13. The ophthalmologic apparatus according to claim 11, wherein alignment in a back-and-forth direction is performed based on a signal of a joystick when the output result of the imaging unit satisfies the predetermined condition.

14. An control method for an ophthalmologic apparatus including an anterior eye illumination unit configured to illuminate an anterior eye portion of a subject's eye, and a light flux regulation unit provided in an optical path of an imaging optical system for imaging the anterior eye portion of the subject's eye, the control method comprising:
retracting the light flux regulation unit to the outside of the optical path when an output result of an imaging unit, which is provided in the optical path of the imaging optical system, satisfies a predetermined condition.

15. A non-transitory computer-readable storage medium storing a program that causes a computer to perform the control method according to claim 14.

16. An ophthalmologic apparatus comprising:
an acquisition unit configured to acquire information specific to a subject's eye;
a projection unit configured to project a light flux for alignment onto a cornea of the subject's eye;
an anterior eye illumination unit configured to illuminate an anterior eye portion of the subject's eye;
a light flux regulation unit configured to regulate a light flux provided in an optical path of an imaging optical system for imaging the anterior eye portion of the subject's eye;
a drive unit configured to drive the acquisition unit with respect to the subject's eye based on a positional relationship of an image of the light flux, which has been reflected by the cornea of the subject's eye and regulated by the light flux regulation unit; and
a drive control unit configured to control the driving unit to stop driving of the acquisition unit in a back-and-forth direction and to maintain driving of the acquisition unit in right-and-left and up-and-down directions when an output result of an imaging unit, which is provided in the optical path of the imaging optical system, satisfies a predetermined condition.

17. The ophthalmologic apparatus according to claim 16, wherein an intensity of at least an image of the light flux does not reach a threshold when the output result of the imaging unit satisfies the predetermined condition.

18. The ophthalmologic apparatus according to claim 16, wherein alignment in a back-and-forth direction is performed based on a signal of a joystick when the output result of the imaging unit satisfies the predetermined condition.

19. A control method for an ophthalmologic apparatus including an acquisition unit configured to acquire information specific to a subject's eye, a projection unit configured to project a light flux for alignment onto a cornea of the subject's eye, an anterior eye illumination unit configured to illuminate an anterior eye portion of the subject's eye, a light flux regulation unit configured to regulate a light flux provided in an optical path of an imaging optical system for imaging the anterior eye portion of the subject's eye, and a drive unit configured to drive the acquisition unit with respect to the subject's eye based on a positional relationship of an image of the light flux, which has been reflected by the cornea of the subject's eye and regulated by the light flux regulation unit, the control method comprising:
controlling the driving unit to stop driving of the acquisition unit in a back-and-forth direction and to maintain driving of the acquisition unit in right-and-left and up-and-down directions when an output result of an imaging unit, which is provided in the optical path of the imaging optical system, satisfies a predetermined condition.

20. A non-transitory computer-readable storage medium storing a program that causes a computer to perform the control method according to claim 19.

* * * * *